(12) United States Patent
Ou et al.

(10) Patent No.: US 8,232,314 B2
(45) Date of Patent: Jul. 31, 2012

(54) COMPOUNDS THAT PROTECT AGAINST SENSORY HAIR CELL DEATH

(75) Inventors: Henry C. Ou, Seattle, WA (US); Felipe Santos, Seattle, WA (US); Edwin W. Rubel, Seattle, WA (US); David W. Raible, Seattle, WA (US); Julian A. Simon, Seattle, WA (US)

(73) Assignees: University of Washington, Seattle, WA (US); Fred Hutchinson Cancer Research Center, Seattle, WA (US)

( * ) Notice: Subject to any disclaimer, the term of this patent is extended or adjusted under 35 U.S.C. 154(b) by 1077 days.

(21) Appl. No.: 12/014,470

(22) Filed: Jan. 15, 2008

(65) Prior Publication Data

US 2009/0023751 A1 Jan. 22, 2009

Related U.S. Application Data

(62) Division of application No. 11/359,161, filed on Feb. 22, 2006, now abandoned.

(60) Provisional application No. 60/655,463, filed on Feb. 22, 2005.

(51) Int. Cl.
*A01N 43/12* (2006.01)
(52) U.S. Cl. ..................................................... 514/443
(58) Field of Classification Search .................. None
See application file for complete search history.

(56) References Cited

U.S. PATENT DOCUMENTS

| | | | |
|---|---|---|---|
| 5,140,030 A | 8/1992 | Christensen et al. | |
| 5,436,134 A | 7/1995 | Haugland et al. | |
| 5,534,416 A | 7/1996 | Millard et al. | |
| 5,656,449 A | 8/1997 | Yue et al. | |
| 5,658,751 A | 8/1997 | Yue et al. | |
| 6,656,449 B1 | 12/2003 | Serbedzija et al. | |
| 6,664,047 B1 | 12/2003 | Haugland et al. | |
| 2006/0058522 A1 | 3/2006 | Faull et al. | |

FOREIGN PATENT DOCUMENTS

WO   WO 2005/023818   3/2005

OTHER PUBLICATIONS

Ylikoski et al., Hearing Research, 2002, 166: 33-41.*
Baxter et al., Bioorganic & Medicinal Chemistry Letters, 2004, 14: 2817-2822.*
Guan et al., Journal of Combinatorial Chemistry, 2000, 2: 297-300.*
Ruckle et al., J. Med. Chem., 2004, 47: 6921-6934.*
Owens et al., PLOS Genetics, 2008, 4: 1-14.*
Grant, et al., "Regulation of Latent Sensory Hair Cell Precursors by Glia in the Zebrafish Lateral Line", Neuron (2005) 45:69-80.
Harris, et al., "Neomycin-Induced Hair Cell Death and Rapid Regneration in the Lateral Line of Zebrafish", J. Assoc. Res Otolaryngol (2003) 4:219-234.
Seiler, et al., "Defective Calmodulin-Dependent Rapid Apical Endocytosis in Zebrafish Sensory Hair Cell Mutants" J. Neurobiol (1999) 41:424-434.
Smith, et al., "Controlled Comparison of Amikacin and Gentamicin", J of Medicine, (1977) 296:349-53.
Walker et al., "Nephrotoxic and Ototoxic Agents", Clinics in Laboratory Medicine (1990) 10(2):323-354.
Owens et al., Abstracts from the 27th Annual Meeting of the Association for Research in Otolaryngology, Feb. 21-26, 2004, Abstract No, 187, p. 63.
Parng et al., Assay and Drug Development Techniques, 2002, 1:41-48.
Idziorek et al., J Immunol Methods, 1995, 185:249-258.
Cuevas et al., Neurol Res, 2003, 25:271-274.

* cited by examiner

*Primary Examiner* — Ileana Popa
(74) *Attorney, Agent, or Firm* — Karen S. Canady; canady + lortz LLP

(57) ABSTRACT

The present invention provides methods of identifying compounds that protect against ototoxicity induced by one or more noxious stimuli, and methods of treating an individual with compounds identified using the present screening methods. Also provided are compounds demonstrated to have otoprotective effects.

15 Claims, 8 Drawing Sheets

A

2-{{({2,2,2-trichloro-1-[(3-methylbenzoyl)amino]ethyl}amino)carbonothioyl]amino}-4,5,6,7-tetrahydro-1-benzothiophene-3-carboxamide

B 2-({[(4-chlorophenyl)amino]carbonyl}amino)-4,5,6,7-tetrahydro-1-benzothiophene-3-carboxamide

C

2-[(4-chloro-3-nitrobenzoyl)amino]-4,5,6,7-tetrahydro-1-benzothiophene-3-carboxamide

D

2-[(1-piperidinylacetyl)amino]-4,5,6,7-tetrahydro-1-benzothiophene-3-carboxamide

COMPOUNDS THAT PROTECT AGAINST SENSORY HAIR CELL DEATH

This application is a divisional of application Ser. No. 11/359,161, filed Feb. 22, 2006, which claims the benefit of provisional application Ser. No. 60/655,463, filed Feb. 22, 2005, the entire contents of each of which are incorporated herein by reference.

STATEMENT AS TO RIGHTS TO INVENTIONS MADE UNDER FEDERALLY SPONSORED RESEARCH AND DEVELOPMENT

This invention was made with government support under grant numbers F32 DC007224 and R01 DC005987 awarded by the National Institutes of Health. The government may have certain rights in this invention.

BACKGROUND OF THE INVENTION

Aminoglycosides are clinically used drugs that cause dose-dependent sensorineural hearing loss (Smith et al., *New Engl J Med*, (1977) 296:349-53) and are known to kill hair cells in the mammalian inner ear (Theopold, *Acta Otolaryngol* (1977) 84:57-64). In the U.S. over 2,000,000 people receive treatment with aminoglycosides per year. The clinical efficacy of these drugs in treating resistant bacterial infections and their low cost globally account for their continued use and need. Cisplatin, a chemotherapeutic agent is also used for its benefit to life despite its toxic effects on the hair cells of the inner ear. High frequency hearing loss (>8 kHZ) has been reported to be as high as 90% in children undergoing cisplatin therapy (Allen, et al, *Otolaryngol Head Neck Surg* (1998) 118:584-588). The incidence of vestibulotoxic effects of such drugs on patient populations has been less well studied. Estimates range between 3% and 6% with continued reports in the literature of patients with aminoglycoside induced vestibulotoxicity (Dhanireddy et al., *Arch Otolarngol Head Neck Surg* (2005) 131:46-48). Other clinically important and commonly used drugs also have documented ototoxic effects, including loop diuretics (Greenberg, *Am J Med Sci*, (2000) 319:10-24), antimalarial sesquiterpene lactone endoperoxides (i.e., artemesinins) (Toovey and Jamieson, *Trans R Soc Trop Med Hyg* (2004) 98:261-7), antimalarial quinines (Claessen, et al., *Trop Med Int Health*, (1998) 3:482-9), salicylates (Matz, *Ann Otol Rhinol Laryngol Suppl* (1990) 148:39-41), and interferon polypeptides (Formann, et al., *Am J Gastroenterol* (2004) 99:873-77).

Zebrafish are an advantageous animal model for studying hair cell development and function (see, Grant et al., *Neuron* (2005) 45:89-80). U.S. Pat. No. 6,656,449 discloses general methods of screening unknown agents in zebrafish for cell death activity, but does not describe preferential labeling of any particular tissue or cell type in a live zebrafish. Idziorek, et al., disclose that the cell impermeant nuclear dye YOPRO-1 (Molecular Probes, Eugene, Oreg.) does not interfere with cell viability of human immune cells, but does not disclose labeling zebrafish or hair cells. Harris, et al., disclose exposing zebrafish lateral hair cells labeled with the fluorescent vital dye DASPEI to neomycin and identifying regenerating hair cells (*J Assoc Res Otolaryngol* (2003) 4:219-34). Harris, et al., assert to have provided a preparation for studying and identifying genes that influence vertebrate hair cell death. None of the foregoing references disclose using zebrafish for screening for compounds that inhibit or prevent ototoxicity induced by one or more noxious stimuli. Accordingly, there remains a need for the identification of compounds that can counteract sensory hair cell loss. The present invention fulfills this and other needs.

BRIEF SUMMARY OF THE INVENTION

The present invention provides a methods for identifying compounds that decrease, inhibit or prevent sensory hair cell damage or death induced by one or more noxious stimuli, the methods comprising:
 a) preferentially labeling the lateral line hair cells of zebrafish in comparison to other cells, wherein the labeling is substantially non-toxic to the zebrafish hair cells, wherein said label is detectably distinct in a live cell in comparison to a dying cell or a dead cell;
 b) contacting the zebrafish with a test compound suspected of decreasing, inhibiting or preventing sensory hair cell damage or death;
 c) contacting the zebrafish with one or more noxious stimuli, each known to cause sensory hair cell damage or death; and
 d) detecting the label, wherein a compound that decreases, inhibits or prevents sensory hair cell damage or death is identified when the number of live lateral line hair cells is greater in zebrafish contacted with the test compound in comparison to a control zebrafish not contacted by the test compound.

In certain embodiments, the methods include the step of washing away label unassociated with the lateral line hair cells of a zebrafish before contacting a zebrafish hair cell with a test compound.

In certain embodiments, the noxious stimulus comprises one or more drugs known to cause sensory hair cell death. In certain embodiments the noxious stimulus is a sound pressure level (decibel level) known to cause sensory hair cell damage or death. In certain embodiments the noxious stimulus is age.

The methods also include simultaneously screening a plurality of test compounds potentially capable of decreasing, inhibiting or preventing sensory hair cell damage or death induced by one or more noxious stimuli under high throughput conditions. Accordingly, the invention further provides high throughput methods of screening comprising:
 a) labeling the lateral line hair cells of members of a plurality of zebrafish, wherein said labeling preferentially labels lateral line hair cells in comparison to other cells of the zebrafish, wherein said labeling is substantially non-toxic to the zebrafish hair cells, and wherein said label is detectably distinct in a live cell in comparison to a dying cell or a dead cell;
 b) contacting each member of the plurality of zebrafish with one member of a plurality of test compounds suspected of decreasing, inhibiting or preventing sensory hair cell damage or death;
 c) contacting each member of the plurality of zebrafish with one or more noxious stimuli known to cause sensory hair cell damage or death; and
 d) detecting the label in each member of the plurality of zebrafish, wherein a compound that decreases, inhibits or prevent sensory hair cell damage or death is identified when the number of live lateral line hair cells is greater in zebrafish contacted with the test compound in comparison to a control zebrafish not contacted by the test compound.

In addition, the invention provides several compounds identified by the methods of the invention to be protective against ototoxic drugs. These compounds include cepharanthine, amsacrine, drofenine, phenoxybenzamine, N,N-hexamethyleneamiloride, carvedilol and 9-amino-1,2,3,4-tetrahydroacridine. Also identified by the methods of the invention as protective against ototoxic drugs are compounds that contain a thiophene carboxamide moiety (Formula I or II) or a urea-thiophene-carboxamide moiety (Formula III or IV), and are structurally consistent with a drug-like profile, according to Lipinski's Rule of 5 criteria. These compounds include F5, H10, and Compounds A, B, C and D described herein.

The invention further includes methods for decreasing, inhibiting or preventing ototoxicity induced by one or more noxious stimuli by administering a sufficient amount of a compound identified by the screening methods described herein.

BRIEF DESCRIPTION OF THE DRAWINGS

FIG. 1A depicts 5 days post fertilization (dpf) larvae hair cells labeled with FM 1-43 (red) to identify the cytoplasm of hair cells and Yo-Pro-1 (green) labeling the nucleus. After 1 hour exposure to 200 µM, neomycin hair cells that are not protected undergo apoptotic death. Cytoplasmic (red) and nuclear fragments (green) are visible in FIG. 1B.

DETAILED DESCRIPTION OF THE INVENTION

Figure 1B:
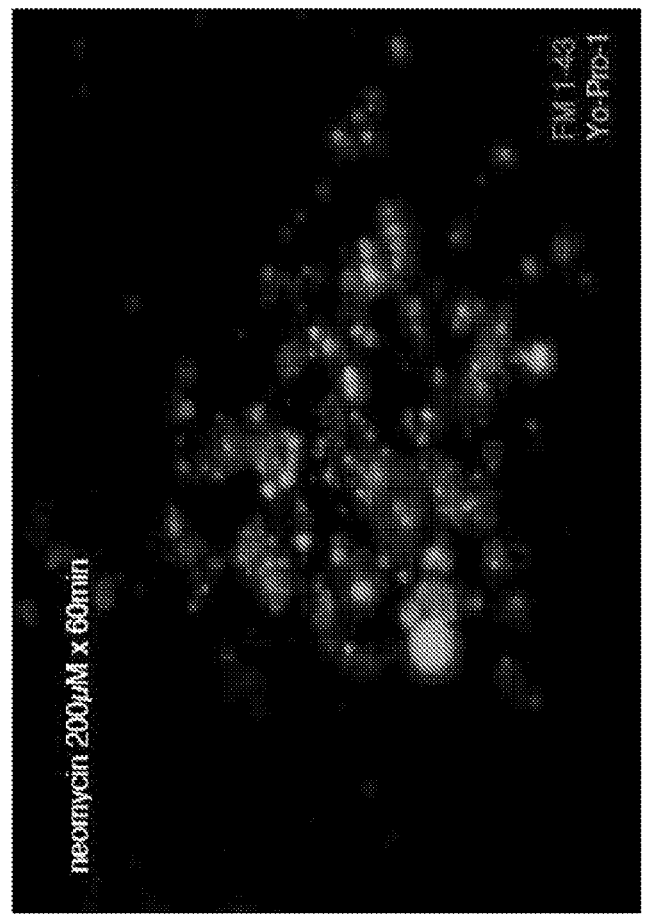
FIGS. 1A and 1B illustrate labeling and neomycin-induced hair cell death of zebrafish lateral line hair cells.

Methods of using a zebrafish model system to screen for small molecules capable of decreasing, inhibiting or preventing sensory hair cell damage or death are provided. Zebrafish are an advantageous animal model system for studying causes and prevention of hearing loss in comparison to mammalian animal model systems. The relative inaccessibility of hair cells in mammalian organisms limits their use as a high throughput model for identifying compounds that would prevent toxin mediated and other forms of hair cell death from occurring. The lateral line hair cells of zebrafish (*Danio rerio*) are structurally and functionally similar to mammalian sensory hair cells. The zebrafish is therefore an ideal model organism for in vivo high throughput screening to identify compounds that can prevent hair cell damage or death from occurring.

The methods are exemplified by screening a combinatorial chemical library for compounds that counteract (i.e., decrease, prevent or inhibit) damage or death to the lateral line hair cells of zebrafish induced by one or more noxious stimuli (i.e., an ototoxic drug, a damaging sound pressure level, presbyacusis or age-related hearing loss). Using this approach, six structurally related small molecules have been identified as protective against the toxic effects of an exemplified aminoglycoside (neomycin) and an exemplified platinum coordination complex (cisplatin) on hair cells. The identified compounds:

F5: 2-({[(4-chlorophenyl)amino]carbonyl}amino)-6-ethyl-4,5,6,7-tetrahydrothieno[2,3-c]pyridine-3-carboxamide:

H10: 2-{[({2,2,2-trichloro-1-[(4-methoxybenzoyl)amino]ethyl}amino)carbonothioyl]amino}-4,5,6,7-tetrahydro-1-benzothiophene-3-carboxamide;

Compound A: 2-{{({2,2,2-trichloro-1-[(3-methylbenzoyl)amino]ethyl}amino)carbonothioyl]amino}-4,5,6,7-tetrahydro-1-benzothiophene-3-carboxamide;

Compound B: 2-({[(4-chlorophenyl)amino]carbonyl}amino)-4,5,6,7-tetrahydro-1-benzothiophene-3-carboxamide;

Compound C: 2-[(4-chloro-3-nitrobenzoyl)amino]-4,5,6,7-tetrahydro-1-benzothiophene-3-carboxamide; and Compound D: 2-[(1-piperidinylacetyl)amino]-4,5,6,7-tetrahydro-1-benzothiophene-3-carboxamide each contain a thiophene carboxamide and are structurally consistent with a drug-like profile, according to Lipinski's Rule of 5 criteria. The methods find use in screening further chemical libraries for additional compounds and in refining identified lead compounds to optimize their protective efficacy.

In addition, the high throughput screening method of the invention has been used to identify several compounds approved by the United States Food and Drug Administration (FDA) as protective against ototoxic drugs. These compounds include cepharanthine, amsacrine, drofenine, phenoxybenzamine, N,N-hexamethyleneamiloride, carvedilol and 9-amino-1,2,3,4-tetrahydroacridine.

DEFINITIONS

As used herein "larva" or "larvae" or "larval" refers to the developmental stage of an organism, including fish and amphibians, that is between an embryo and an adult (Generally reviewed in Gilbert, *Developmental Biology*, 6th Ed., 2000, Sinauer Associates, Inc., Sunderland, Mass.).

As used herein, the terms "drug-induced ototoxicity" or "drug-induced sensory hair cell death" refers to damage or death in a sensory hair cell caused by one or more pharmacological agents. Damage or death in a sensory hair cell can be determined using the assays described in the examples below.

As used herein, a "condition associated with sensory hair cell death" refers to drug-induced ototoxicity, noise-induced hearing loss and/or age-related hearing loss.

As used herein, an "ototoxic drug" or a "drug that induces ototoxicity" or a "drug having an ototoxic activity or effect" interchangeably refer to a pharmacological agent that causes damage or death to a sensory hair cell.

As used herein, a "noxious stimulus," or a "noxious stimuli," refers to any kind of stimulus that induces damage or death to a sensory hair cell. A noxious stimulus can be extracellular or intracellular. A noxious stimulus can include, and is not limited to, a chemical compound (i.e., an ototoxic pharmacological agent or a chemical toxin), a damaging sound pressure or decibel level, or age (presbycusis, or age-related hearing loss).

As used herein, the term "vital dye" refers to any dye, that when taken up by a cell, does not substantially cause cell death or damage.

The "Lipinski Rule of 5" criteria in determining the identification of a "drug-like" compound predicts that poor absorption or permeation is more likely when there are more than 5H-bond donors, 10H-bond acceptors, the molecular weight is greater than 500 and the calculated Log P (C Log P) is greater than 5 (or M log P>4.15) (see, Lipinski, et al., *Adv Drug Deliv Rev*, (2001) 46:3-26, hereby incorporated herein by reference).

As used herein, "treatment" refers to prophylaxis and/or therapy.

As used herein, "prevent" means to hinder, reduce, or delay the onset of a condition.

As used herein, "a" or "an" means one or more, unless clearly indicated otherwise.

DETAILED EMBODIMENTS

The present invention provides methods for identifying compounds that decrease, inhibit or prevent sensory hair cell death induced by one or more noxious stimuli, the methods comprising:
a) preferentially labeling the lateral line hair cells of a zebrafish in comparison to other cells, wherein the labeling is substantially non-toxic to the zebrafish hair cells, wherein said label is detectably distinct in a live cell in comparison to a dying cell or a dead cell;
b) contacting the zebrafish with a test compound suspected of decreasing, inhibiting or preventing sensory hair cell death;
c) contacting the zebrafish with one or more noxious stimuli known to cause sensory hair cell death; and
d) detecting the label, wherein a compound that decreases, inhibits or prevents sensory hair cell death is identified when the number of live lateral line hair cells is greater in zebrafish contacted with the test compound in comparison to a control zebrafish not contacted by the test compound.

In certain embodiments, the methods include the step of washing away label unassociated with the lateral line hair cells of a zebrafish before contacting a zebrafish hair cell with a test compound.

In one embodiment, the methods identify compounds that decrease, inhibit or prevent cell death or damage in inner ear sensory hair cells, for example, in the inner ear of a mammal.

In certain embodiments, the noxious stimulus comprises a pharmacological agent (i.e., drug) known to induce sensory hair cell damage or death. Usually the noxious stimulus is extracellular, in certain embodiments, the noxious stimulus comprises a sound pressure level or decibel level known to cause sensory hair cell damage or death. In some embodiments, the noxious stimulus is intracellular. For instance, the pathophysiology of noise-induced hearing loss overlaps with the multifactoral process of age-related hearing loss (i.e., presbyacusis), and further shares some of the pathological hallmarks of hearing loss mediated by ototoxic compounds. The molecular mechanisms of age-related hearing loss are reviewed in, for example, Seidman, et al., *Ageing Res Rev* (2002) 3:331-43; Gratton and Vazquez, *Curr Opin Otolaryngol Head Neck Surg* (2003) 11:387-71; and Seidman, et al., *Acta Otolaryngol Suppl* (2004) 552:16-24, the disclosures of which are hereby incorporated herein by reference. Accordingly, in certain embodiments, the noxious stimulus is age. The methods test for sensory hair cell death mediated by both or either programmed cell death (apoptosis) and/or cell disintegration (necrosis).

Those of skill in the art will further recognize that renal cells share many of the same toxicities associated with hair cell death (reviewed in Humes, *Ann NY Acad Sci* (1999) 884:15-18; and Walker et al., *Clin Lab Med* (1990) 10:323-354). For instance, loop diuretics, aminoglycosides, and platinum coordination complexes can induce both nephrotoxicity and ototoxicity. Accordingly, the present screening methods identify compounds that decrease, inhibit or prevent death or damage in sensory hair cells and/or renal cells.

The methods usually employ zebrafish larvae, typically at 6 or fewer days post fertilization (dpf) so that they can still be kept in minimal volumes for testing (e.g., as little as 100 μl). Zebrafish larvae can be used as early as the lateral line hair cells are developed, but are usually used after 4 dpf, so that the hair cells are susceptible to sensory hair cell damage or death in response to a noxious stimulus. Typically, the methods are carried out on zebrafish larvae that are about 5 dpf. The precise stage of development of the zebrafish larvae is not critical to the success of the methods, so Song as the lateral Sine hair cells are developed and susceptible to the effects of ototoxic pharmacological agents, and the larvae are still of a size convenient for use in screening (i.e., they can be kept in the well of a multiwell plate of a desired size). Zebrafish development is reviewed in detail in *Methods in Cell Biology: The Zebrafish Cellular and Developmental Biology*, Detrich, Zon and Westerfield. Eds., 2004, Academic Press, the disclosure of which is hereby incorporated herein by reference.

Zebrafish are commercially available for purchase, for example through WARD'S Natural Science (available through their worldwide website at wardsci.com) and from the Zebrafish International Resource Center (available through their worldwide website at zfin.org/zirc/home/stckc-tr.php). Housing systems for raising zebrafish are available through Aquatic Habitats in Apopka, Fla. Information on breeding and raising zebrafish can be found through the Zebrafish Information Network, on the worldwide web at zfin.org, and in Detrich and Zon, *Zebrafish: Biology*, 1998, Academic Press; *Zebrafish: A Practical Approach*, Nusslein-Volhard and Dahm, Eds., 2002, Oxford University Press, and in Westerfield, *The Zebrafish Book: A Guide for the Laboratory Use of Zebrafish (Danio rerio)*, 1995, Institute of Neuro Science, the disclosures of each of which are hereby incorporated herein by reference.

Preferential Labeling of Zebrafish Lateral Line Sensory Hair Cells

Surprisingly, the lateral line hair cells of a zebrafish conveniently can be specifically labeled. Accordingly, the present methods involve specifically labeling the lateral line hair cells of a zebrafish such that the lateral line hair cells are preferentially labeled in comparison to other cells in the zebrafish larvae. This can be accomplished in several ways, including limiting the exposure of the larvae to the one or more labels used, and/or rinsing away label unassociated with the labeled sensory hair cells. The particular exposure time of zebrafish larvae to the one or more labels is not critical, so long as the exposure time is sufficient to detectably label the lateral line hair cells without substantially labeling other cell types. Actual exposure times will depend on the particular label or labels used, but can be as short as 15, 30, 45 or 60 seconds, and could be as long as 15, 30, 45 or 60 minutes, and could be shorter or longer, as required. When labeling a zebrafish with more than one label, the first label and the second label can be added sequentially or simultaneously. For instance, a zebrafish can be exposed to a cytoplasmic vital dye for about 15, 30, 45 or 60 seconds, and then subsequently exposed to a nuclear vital dye for about 15, 30, 45 or 60 minutes. Label can be added to the zebrafish media before or after one or more zebrafish are placed in the media. Normally, the label is dissolved in a minimum amount of zebrafish media or another compatible solution before adding to the zebrafish media.

The labels used in the present methods are detectably distinct in a live cell versus a dead or dying cell. Lateral line hair cell death can be detected in vivo or in vitro using microscopy techniques well known in the art, particularly detection techniques used by standard microplate readers (i.e., fluorescence, chemiluminescence, colorimetry). Preferably, the lateral line hair cells are labeled such that a distinction between cell viability and cell death or damage can be directly detected, without first fixing the cells or the organism. Usually, the one or more labels are fluorescent labels. When using more than one fluorescent label, for instance to label multiple and distinct compartments of a cell, the fluorescent labels should have detectably distinct emission spectra.

In one embodiment, the methods involve preferentially labeling the lateral line hair cells of a zebrafish with one or more fluorescent vital dyes, each of which does not cause substantial damage or death to viable, labeled cells, in one embodiment, the lateral line hair cells are labeled with a cytoplasmic vital dye and a nuclear vital dye. Simultaneous labeling of the cytoplasm and the nucleus of the lateral line hair cells allows for more detailed and earlier detection of sensory hair cell death or damage, that would not be recognized as well by using either a cytoplasmic dye or a nuclear dye alone. The particular dye or dyes used is not critical to the success of the present methods, as long as the labels differentiate between live cells and dead or damaged cells without substantially affecting viability of labeled cells.

Cytoplasmic vital dyes of use in the present invention allow detection of the integrity of a cell cytoplasm. Many cytoplasmic dyes are lipophilic dyes that attach to or integrate into external or internal cell membranes, including the plasma membrane, the endoplasmic reticulum, the Golgi apparatus and mitochondria. Of particular interest are cytoplasmic dyes that attach to or integrate into the plasma membrane, without substantially affecting cell viability. The particular cytoplasmic vital dye used is not critical to the success of the present methods. Exemplified cytoplasmic dyes include lipophilic carbocyanine dyes and aminostyryl dyes, presently used in neuronal tracing. Of particular interest are aminostyryl dyes and so-called "FM® dyes," commercially available through Molecular Probes, Inc. (Eugene Oreg.). Detailed information about dyes and dye products can be found in Haugland, (2002) *Handbook of Fluorescent Probes and Research Products,* 9th Edition, a combined handbook and catalog published by Molecular Probes and available on the worldwide web at probes.com.

"FM® dyes" of use in the present invention include:
N-(3-triethylammoniumpropyl)-4-(4-(dibutylamino)styryl) pyridinium dibromide, (FM 1-43);
N-(3-triethylammoniumpropyl)-4-(6-(4-(diethylamino)phenyl)hexatrienyl)pyridinium dibromide, (FM 4-84);
N-(3-triethylammoniumpropyl)-4-(4-(diethylamino)styryl) pyridinium dibromide, (FM 2-10);
N-(3-triethylammoniumpropyl)-4-(4-(dipentylamino)styryl) pyridinium dibromide, (FM 1-84); and
N-(3-trimethylammoniumpropyl)-4-(6-(4-(diethylamino) phenyl)hexatrienyl)pyridinium dibromide, (FM 5-95).

Other commercially available cytoplasmic dyes of use in practicing the present methods include:
N-(3-triethylammoniumpropyl)-4-(4-(4-(diethylamino)phenyl)butadienyl) pyridinium dibromide, (RH 414); and
2-(4-(dimethylamino)styryl)-N-ethylpyridinium iodide (DASPEI).

Nucleic acid staining vital dyes for use in the present methods include cell-membrane-permeant and cell-membrane impermeant cyanine nucleic acid stains, also commercially available from Molecular Probes, Inc. Usually the methods employ membrane impermeant cyanine nucleic acid stains, including cyanine monomers and cyanine dimers. Of particular interest are quinolinium cyanine nucleic acid stains, both monomer and dimer. Quinolinium cyanine nucleic acid stains are described in U.S. Pat. Nos. 6,664,047; 5,658,751; 5,656, 449; 5,534,416; 5,436,134; 5,410,030. The particular nuclear vital dye is not critical to the success of the present methods, as long as it is detectably distinct between live and dead or dying cells, it does not substantially affect cell viability, and does not require cell permeabilization for nuclear staining.

Usually, a cyanine monomer nucleic acid staining dye is used. Exemplified cyanine monomers include:
benzoxazolium, 3-methyl-2-[[1-[3-(trimethylammonio)propyl]-4(1H)pyridinylidene]methyl]-, diiodide, PO-PRO™-1.
benzothiazolium, 3-methyl-2-[[1-[3-(trimethylammonio) propyl]-4(1H)-pyridinylidene]methyl]-, diiodide, BO-PRO™-1;
benzoxazolium, 3-methyl-2-[3-[1-[3-(trimethylammonio) propyl]-4(1H)-pyridinylidene]-1-propenyl]-, diiodide, PO-PRO™-3;
benzothiazolium, 3-methyl-2-[3-[1-[3-(trimethylammonio) propyl]-4-(1H)-pyridinylidene]-1-propenyl]-, diiodide, BO-PRO™-3;
quinolinium, 4-[(3-methyl-2(3H)-benzoxazolylidene)methyl]-1-[3-(trimethylammonio)propyl]-, diiodide, YO-PRO®-1;
quinolinium, 4-[(3-methyl-2(3H)-benzothiazolylidene)methyl]-1-[3-(trimethylammonio)propyl]-, diiodide, TO-PRO®-1;
quinolinium, 4-[3-(3-methyl-2(3H)-benzoxazolylidene)-1-propenyl]-1-[3-(trimethylammonio)propyl]-, diiodide, YO-PRO®-3; and
quinolinium, 4-[3-(3-methyl-2(3H)-benzothiazolylidene)-1-propenyl]-1-[3-(trimethylammonio)propyl]-, diiodide, TO-PRO®-3. Further cyanine monomer nucleic acid staining dyes are available from Molecular Probes, inc.

In certain embodiments, a cyanine dimer nucleic acid staining dye is used. Exemplified cyanine dimers include:
benzoxazolium, 2,2'-[1,3-propanediylbis[(dimethyliminio)-3,1-propanediyl-1(4H)-pyridinyl-4-ylidenemethylidyne]] bis[3-methyl]-, tetraiodide, POPO™-1;
benzoxazolium, 2,2'-[1,3-propanediylbis[(dimethyliminio)-3,1-propanediyl-1(4H)-pyridinyl-4-ylidenemethylidyne]]bis[3-methyl]-, tetraiodide, BOBO™-1;
benzoxazolium, 2,2'-[1,3-propanediylbis[(dimethyliminio)-3,1-propanediyl-1(4H)-pyridinyl-4-ylidene-1-propen-1-yl-3-ylidene]]bis[3-methyl]-, tetraiodide, POPO™-3;
benzothiazolium, 2,2'-[1,3-propanediylbis[(dimethyliminio)-3,1-propanediyl-1(4H)-pyridinyl-4-ylidene-1-propen-1-yl-3-ylidene]]bis[3-methyl]-, tetraiodide, BOBO™-3;
quinolinium, 1,1'-[1,3-propanediylbis[(dimethyliminio)-3,1-propanediyl]]bis[4-[(3-methyl-2(3H)-benzoxazolylidene) methyl]]-, tetraiodide, YOYO®-1;
quinolinium, 1-1'-[1,3-propanediylbis[(dimethyliminio)-3, 1-propanediyl]]bis[4-[(3-methyl-2(3H)-benzothiazolylidene)methyl]]-, tetraiodide, TOTO®-1;
quinolinium, 1,1'-[1,3-propanediylbis[(dimethyliminio)-3,1-propanediyl]]bis[4-[3-(3-methyl-2(3H)-benzoxazolylidene)-1-propenyl]]-, tetraiodide, YOYO®-3;
quinolinium, 1,1'-[1,3-propanediylbis[(dimethyliminio)-3,1-propanediyl]]bis[4-[3-(3-methyl-2(3H)-benzothiazolylidene)-1-propenyl]]-, tetraiodide, TOTO®-3. Further cyanine dimer nucleic acid staining dyes are available from Molecular Probes, Inc.

In certain embodiments, the presence or absence of sensory hair cell death is detected in vitro. Such in vitro cell death detection systems are well known in the art. For instance, for the detection of programmed cell death (i.e., apoptosis), terminal deoxynucleotide transferase dUTP nick end labeling (TUNEL) assays kits are readily available (R & D Systems, Minneapolis, Minn.; Molecular Probes, Eugene, Oreg.; BD Biosciences, Palo Alto, Calif.; and Phoenix Flow Systems, San Diego, Calif.). Commercially available kits can also be purchased for the detection of cell disintegration (i.e., necrosis) (Promega, Madison, Wis.; Molecular Probes, Eugene Oreg.). The distinction between necrotic and apoptotic cell death is reviewed in Chapter 17 of *Molecular Biology of the Cell*, 4th Edition, Alberts, Johnson, Lewis, Raff, Roberts and Walter, Eds., 2002 Garland Publishing, NY, the disclosure of which is hereby incorporated herein by reference. Secondary antibodies used in detecting markers of cell death in fixed tissues allow for use of all kinds of detectable moieties known in the art, including enzymes, radioactive isotopes, and fluorescent labels.

Test Compounds

The present methods involve contacting a zebrafish with a test compound suspected of decreasing sensory hair cell death. Depending on the particular assay, a test compound can be added before, concurrently or after exposing a zebrafish to a noxious stimulus known to cause ototoxicity. The time period of exposure to the test compound is not critical to the success of the methods. A selected time period of exposure should be sufficient to detect any protective effects, but not so long so as to introduce unnecessary inefficiencies into the screening methods. Usually, an optimized time period of exposure to one or more test compounds is empirically determined, in certain embodiments, the zebrafish are exposed to the test compound about 15, 30, 45, or 60 minutes prior to being exposed to one or more noxious stimuli. In certain embodiments, the zebrafish are contacted with a test compound concurrently with exposure to the one or more noxious stimuli. In certain embodiments, the zebrafish are contacted with a test compound after exposure to the one or more noxious stimuli.

In preferred embodiments, the assays are designed to screen large chemical libraries by automating the assay steps and providing compounds from any convenient source to assays, which are typically run in parallel (e.g., in microtiter formats on microtiter plates in robotic assays). The chemical libraries can be completely random, or comprise members that contain a core structure based on one or more promising lead compounds (i.e., a thiophene-carboxamide core structure). The chemical libraries can be completely synthetic or can include some or all members that are derived from naturally occurring sources, including, for example, bacteria, fungi, plants, insects and vertebrate (i.e., *Xenopus* (frog) or *Anguilla* (eel)) and non-vertebrate animals (i.e., *Strongylocentrotus* (sea urchin) or mollusks).

Essentially any chemical compound can be tested as a potential inhibitor of sensory hair cell damage or death for use in the methods of the invention. Most preferred are generally compounds that can be dissolved in aqueous or organic (especially DMSO-based) solutions and compound which fall within Lipinski's "Rule of 5" criteria. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), as well as providers of small organic molecule libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), and Tripos, Inc. (St. Louis, Mo.).

A combinatorial chemical library is a collection of diverse chemical compounds generated by either chemical synthesis or biological synthesis, by combining a number of chemical "building blocks" such as reagents. For example, a linear combinatorial chemical library such as a small molecule library is formed by combining a set of chemical building blocks in every possible way. Millions of chemical compounds can be synthesized through such combinatorial mixing of chemical building blocks.

Preparation and screening of combinatorial chemical libraries is well known to those of skill in the art. See, for example, U.S. Pat. Nos. 5,683,048; 5,958,792; 8,185,506; 8,541,211; 6,721,665, the disclosures of which are hereby incorporated herein by reference. Preferably, the combinatorial chemical libraries are comprised of members that are "drug-like" compounds, as defined by Lipinski Rule of 5 criteria. Combinatorial chemical libraries based on a core structure of a known pharmacological agent have been constructed (e.g., benzodiazepines (U.S. Pat. No. 5,288,514); oligocarbamates (Cho et al., *Science* 261:1303 (1993)); isoprenoids, (U.S. Pat. No. 5,569,588); thiazoiidinones and metathiazanones (U.S. Pat. No. 5,549,974); pyrrolidines (U.S. Pat. Nos. 5,525,735 and 5,519,134) morpholino compounds (U.S. Pat. Nos. 5,698,685 and 5,506,337). Devices for the preparation of combinatorial libraries are also commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.).

In certain embodiments, the test compound or the members of the combinatorial chemical library will comprise a thiophene-carboxamide moiety core structure of formula I or formula II;

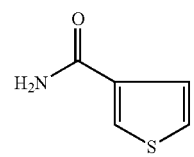

Formula I

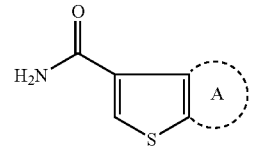

Formula II

As shown in the pharmacophores represented by Formula I and Formula II, a thiophene-carboxamide moiety comprising a core structure of the lead compounds of the invention includes a thiophene functional group linked to a carboxamide functional group. The thiophene functional group can optionally have a ring attached (A), wherein the ring optionally can be 5-7 members, aromatic or non-aromatic, open or dosed, and can contain one or more heteroatoms, including N, O or S. In those species with no ring attached, substituents at the corresponding positions are tolerated. Those of skill in the art will recognize from the pharmacophores represented by Formula I and Formula II, and the representative identified compounds (F5, H10, Compound A, Compound B, Compound C and Compound D) that numerous substitutions can be made on the thiophene-carboxamide core structure while still maintaining drug-like structural features within Lipinski's "Rule of 5" and the desired function of decreasing, inhibiting or preventing sensory hair cell damage or death.

In a further embodiment, the lead compound pharmacophore comprises a urea-thiophene-carboxamide moiety, which includes a urea functional group linked to a thiophene functional group linked to a carboxamide functional group, represented below in Formula III and Formula IV, wherein X is a heteroatom, including N, O or S. The thiophene functional group can optionally have a ring attached (A), wherein the ring optionally can be 5-7 members, aromatic or non-aromatic, open or closed, and can contain one or more heteroatoms, including N, O or S. In those species with no ring attached, substituents at the corresponding positions are tolerated. Those of skill in the art will recognize from the pharmacophores represented by Formula III and Formula IV, and the representative identified compounds (F5, H10, Compound A, Compound B, Compound C and Compound D) that numerous substitutions can be made on the urea-thiophene-carboxamide core structure while still maintaining drug-like structural features within Lipinski's "Rule of 5" and the desired function of decreasing, inhibiting or preventing sensory hair cell damage or death.

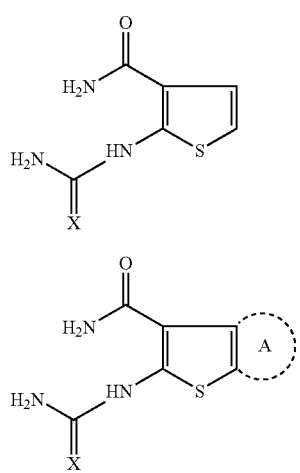

Formula III

Formula IV

Noxious Stimuli Known to Induce Ototoxicity

The present methods involve contacting a zebrafish sensory hair cell with one or more noxious stimuli known to cause sensory hair cell damage or death. The time period for exposure to the noxious stimulus is not critical to the success of the present methods, so long as there is detectable differentiation in the viability of lateral line sensory hair cells between zebrafish treated with both a test compound and exposed to the noxious stimulus and zebrafish exposed to the noxious stimulus only. Usually the time period for exposure to a noxious stimulus known to cause sensory hair cell damage or death is empirically determined. In certain embodiments of the assay, a zebrafish is exposed to a noxious stimulus for about 10, 20, 30, 40 or 50 minutes, as needed before carrying out detection, in certain embodiments, a zebrafish is exposed to a noxious stimulus for about 1 hour, 2 hours, 3 hours, or 4 hours before detection. In embodiments where the noxious stimulus is age, the exposure time can correlate with the lifetime (age) of the zebrafish.

In some embodiments, the noxious stimulus is a sound pressure (decibel (dB)) level known to cause sensory hair cell damage or death. Typically, the decibel level is at least about 85 dB, but decibel levels of at least about 90 dB, 100 dB, 110 dB, 120 dB, 130 dB, 140 dB, 150 dB, 160 dB, 170 dB, 180 dB, 190 dB, 200 dB and greater are known to cause sensory hair cell damage or death.

In some embodiments, the noxious stimulus is a pharmacological agent or drug known to cause sensory hair cell damage or death. In some embodiments, the noxious stimulus is a pharmacological agent or drug known to cause damage or death in a sensory hair cell and/or a renal cell. The noxious stimulus can also be a viral infection or a bacterial infection of the ear.

The particular drug or class of drug applied is not critical to carrying out the present methods, as long as it is established in a positive control that the drug induces sensory hair cell damage or death. As noted above, numerous classes of drugs have been associated with sensory hair cell damage or death, including aminoglycosides, anticancer agents, loop diuretics, sesquiterpene lactone endoperoxides (i.e., artemisinins), salicylates, and interferon polypeptides (reviewed in Palomar, *Acta Otolaryngol*, (2001) 121:569-72; and Matz, *Ann Otol Rhinol Laryngol Suppl*. (1990) 148:39-41).

Aminoglycosides associated with sensory hair cell damage or death include erythromycin, vancomycin, neomycin, gentamicin, streptomycin, kanamycin, tobramycin and amikacin and netilmicin. Ototoxic effects of aminoglycoside drugs are reviewed in *Goodman and Gilman's The Pharmacological Basis of Therapeutics*, 10th Edition, 2001, Hardman, Limbird and Goodman-Gilman, Eds., McGraw-Hill, the disclosure of which is hereby incorporated herein by reference. Teicoplanin is another antibiotic that can induce sensory hair cell death or damage (Bonnet, et al., *Ann Otol Rhinol Laryngol*, (2004) 113:310-12).

The ototoxic effects of aminoglycosides are potentiated by the use of diuretics such as furosemide and ethacrynic acid (see, Goodman and Oilman, supra.) Loop diuretics themselves have been associated with sensory hair cell death or damage (see, Goodmand and Oilman and Matz, supra). Exemplified loop diuretics include furosemide, bumetanide, ethacrynic acid, torsemide, azosemide, muzolimine, piretanide and tripamide.

Numerous anticancer agents have been associated with sensory hair cell damage or death. For instance, platinum coordination complexes associated with sensory hair cell damage or death include cisplatin and carboplatin, with cisplatin exhibiting greater ototoxic side effects than carboplatin. See, Goodman and Oilman, supra. Other anticancer agents have been shown to cause ototoxicity, including difluoromethylornithine (DFMO) (Lao, et al., *Cancer Epidemiol Biomarkers Prev*, (2004) 13:1250-2), nitrogen mustards (i.e., mechlorethamine, cyclophosphamide, ifosfamide, melphalan, and chlorambucil), and vinca alkaloids (i.e., vincristine and vinblastine sulfate) (reviewed in Schweitzer, *Otolaryngol Clin North Am* (1993) 26:759-89).

Anti-malarial drugs have also been associated with ototoxicity, in particular, sesquiterpene lactone endoperoxides (i.e., artemisinins or artemisinin derivatives) (Toovey and Jamieson, *Trans R Soc Trap Med Hyg*) and quinines (Fusetti, et al., *Clin Ter* (1999) 150:379-82; Claessen, et al., *Trop Med Int Health* (1998) 3:482-9; Tange, et al., *Auri Nasus Larynx* (1997) 24:131-6; and Nielsen-Abbring, et al., *ORL J Otorhinolaryngol Relat Spec* (1990) 52:65-8). Exemplified antimalarial endoperoxides include artemisinin, artemether, artesunate, and dihydroartemisinin. Exemplified antimalarial quinine drugs include quinine, chloroquine, amodiaquine, hydroxychloroquine, mefloquine, and primaquine. See, Goodman and Gilman, supra.

Salicylates are a another class of drugs associated with ototoxicity (Mate, supra and Huang, et al., *J Neurophysiol* (Dec. 8, 2004), PubMed ID no, 15590729). Exemplified salicylates include salicylic acid, acetylsalicylic acid (aspirin), methyl salicylate, diflunisal, salsalate, olsalazine, and sulfasalazine. See, Goodman and Gilman, supra.

Administration of interferon polypeptides has also been associated with ototoxicity and sudden hearing loss. Several studies have implicated interferon-alpha2 (IFN-$\alpha$2) therapy with hearing loss (Formann, et al, *Am J Gastroenterol* (2004) 99:873-7; Gorur, et al., *Auris Nasus Larynx* (2003) 30:41-4; and Akyol, et al, *Otolaryngol Head Neck Surg* (2001) 124: 107-10), However, it is not clear that IFN-$\alpha$2-induced hearing loss is due to sensory hair cell damage or death (Akyol, et al., supra).

Detection

Any of a number of techniques can be used for detection of the label, but the particular detection technique employed will depend on the label used, whether the labeling was done in vivo or in vitro, or whether the detection is being performed after the cells have been fixed. Usually, detection can be conveniently carried out in unfixed cells of live zebrafish larvae that were labeled in vivo, for instance by visual inspection or by using a microscope. Typically, the labeling employs one or more fluorescent labels, so the label is detected using fluorometry using techniques well known to those in the art, usually employing a fluorescent microscope, a microplate reader with fluorescent detection capacities, or when appropriate, a flow cytometer. In other embodiments, detection is carried out on fixed cells, in which case the detection technique can include visual inspection, fluorescence detection, colorimetric detection, or radioactivity detection.

The methods seek to identify compounds that decrease, inhibit or prevent sensory hair cell damage or death. A test compound "decreases" or "inhibits" sensory hair cell damage or death when the number of live lateral line sensory hair cells is greater in a zebrafish contacted with that test compound and one or more noxious stimuli known to cause sensory hair cell damage or death (i.e., a known ototoxic drug, a decibel level of at least 85 dB, age) in comparison to a control zebrafish contacted with the one or more noxious stimuli but not contacted with the test compound. Usually the number of live lateral line sensory hair cells will be at least 10-20% greater preferably about 30%, 40% or 50% greater, and more preferably about 60%, 70% or 80% greater. With most preferred compounds the number of live lateral line sensory hair cells is at least 85%, 90%, or 95% greater, or even 100% greater. Preferably, the test compound completely inhibits or prevents sensory hair cell damage or death, in which case the sensory hair cell damage or death induced by the one or more noxious stimuli is nullified.

High Throughput Assay Format

The invention provides assays for the identification of compounds that decrease, inhibit or prevent sensory hair cell damage or death caused by one or more noxious stimuli in a high throughput format. For each of the assay formats described, "no test compound" control reactions which do not include a test compound provide a background level of noxious stimulus-induced sensory hair cell death. In the high throughput assays of the invention, it is possible to screen up to several thousand different test compounds in a single day, in particular, each well of a microtiter plate can be used to run a separate assay against a selected potential test compound, or, if concentration or incubation time effects are to be observed, every 5-10 wells can test a single modulator. Thus, a single standard microtiter plate can assay about 100 (i.e., 96) test compounds If one compound is tested per well. During initial screening runs, it can be more efficient to test as many as 3, 5, 7 or even 10 potential inhibitor compounds in a single well. It is possible to assay 50-100 plates per day or more; assay screens for up to about 6,000-20,000, and even up to about 100,000-1,000,000 different compounds is possible using the integrated systems of the invention.

Using the present screening methods, test compounds can be screened for their ability to decrease or inhibit sensory hair cell damage or death in zebrafish larvae placed in the wells of standard 6-well, 12-well, 24-well, 48-well, and 96-well multiwell culture plates. In larger wells, a greater volume of zebrafish media can be kept in the wells, and more zebrafish larvae can be cultured in a single well. For example, a single zebrafish larva can be kept in as little as 100 µl in a well of a standard 96-well plate (see, U.S. Pat. No. 6,656,449, hereby incorporated herein by reference). The steps of labeling, addition of reagents, fluid changes, and detection are compatible with full automation, for instance using programmable robotic systems or "integrated systems" commercially available, for example, through BioTX Automation, Con roe, TX; Qiagen, Valencia, Calif.; Beckman Coulter, Fullerton, Calif.; and Caliper Life Sciences, Hopkinton, Mass.

Accordingly, the invention provides methods for simultaneously screening a plurality of compounds that potentially decrease, inhibit or prevent sensory hair cell death or damage induced by one or more noxious stimuli, the method comprising:

a) preferentially labeling the lateral line hair cells of a plurality of zebrafish in comparison to other cells of the zebrafish, wherein said labeling is substantially non-toxic to the zebrafish hair cells, wherein said label is detectably distinct in a live cell in comparison to a dying cell or a dead cell;

b) contacting each member of the plurality of zebrafish with one member of a plurality of test compounds suspected of decreasing sensory hair cell death;

c) contacting each member of the plurality of zebrafish with one or more noxious stimuli known to cause sensory hair cell death; and d) detecting the label in each member of the plurality of zebrafish, wherein a compound that decreases, inhibits or prevents sensory hair cell death is identified when the number of live lateral line hair cells is greater in zebrafish contacted with the test compound in comparison to a control zebrafish not contacted by the test compound.

In some embodiments, the high throughput methods further comprise after step a) the step of washing away label unassociated with the lateral line hair cells of the zebrafish.

In some assays, in pilot or high-throughput format, it will be desirable to have positive controls to ensure that the components of the assays are working properly. For example, a known inhibitor of sensory hair cell death or damage induced by one or more noxious stimuli can be incubated with another test compound of the assay, and the resulting increase or decrease in signal determined according to the methods herein.

In one preferred embodiment, potential inhibitors of sensory hair cell death are identified by screening a combinatorial library containing a large number of potential therapeutic test compounds. Such "combinatorial chemical libraries" can be screened in one or more assays, as described herein, to identify those library members (particular chemical species or subclasses) that display a desired characteristic activity, here reduction or elimination of sensory hair cell death. The compounds thus identified can serve as conventional "lead compounds" or can themselves be used as potential or actual therapeutics.

Methods of Treating Sensory Hair Cell Damage or Death

The invention further provides for methods of treating or preventing conditions associated with sensory hair cell death or damage caused by one or more noxious stimuli, the methods comprising administering a sufficient amount of a compound identified by the screening methods set forth above. In some embodiments, the sensory hair cells are inner ear hair cells. In some embodiments, the identified compound is administered before exposure to the one or more noxious stimuli known to cause sensory hair cell death or damage (i.e., prophylactically). In some embodiments, the identified compound is administered at the same time as exposure to the one or more noxious stimuli known to cause sensory hair cell death or damage (i.e., concurrently or concomitantly). In some embodiments, the identified compound is administered after exposure to the one or more noxious stimuli known to cause sensory hair cell death or damage.

In a related aspect, the methods provide for decreasing, inhibiting or preventing conditions associated with sensory hair cell death in an individual in need thereof, by administering a sufficient amount of a compound comprising a thiophene-carboxamide moiety of Formula I or Formula II that exhibits the functional activity of decreasing, inhibiting or preventing noxious stimulus-induced damage or death of the lateral line hair cells of a zebrafish. The protective activity of the administered compound can be measured according to the zebrafish screening assays described herein. In one embodiment, the administered compound comprises a urea-thiophene-carboxamide moiety of Formula III or Formula IV. In one embodiment, the compound is selected from the group consisting of F5, H10, Compound A, Compound B, Compound C and Compound D. In one embodiment, the administered compound comprises cepharanthine, amsacrine, drofenine, phenoxybenzamine, N,N-hexamethyleneamiloride, carvedilol or 9-amino-1,2,3,4-tetrahydroacridine.

Usually the administered compound will decrease or inhibit noxious stimulus-induced death or damage of zebrafish lateral line sensory hair cells in assays of the invention by a detectable amount in comparison to a control assay where the lateral line sensory hair cells are contacted with only a noxious stimulus (i.e., at least about 30% or 40%). More usually, the administered compound will decrease or inhibit noxious stimulus-induced death or damage of lateral line sensory hair cells by at least 50%, 60% or 70%, even at least 80% or 90%, in comparison to a control assay. Preferably, the administered compound will completely inhibit or prevent noxious stimulus-induced death or damage of lateral line sensory hair cells.

The methods are useful in treating or preventing any disease condition associated with sensory hair cell damage or death. Conditions associated with sensory hair cell damage or death are usually caused by a noxious stimulus, either extracellular or intracellular. Such conditions, include, but are not limited to, drug-induced ototoxicity, noise-induced hearing loss, age-related hearing loss, and viral infection or bacterial infection of the ear, in certain embodiments, the methods treat nephrotoxicity correlative with or associated with ototoxicity, in particular, drug-induced ototoxicity.

In some embodiments, the noxious stimulus is a pharmacological agent known to cause sensory hair cell death or damage (i.e., drug-induced ototoxicity). In some embodiments, the noxious stimulus is exposure to a sound pressure or decibel level known to cause sensory hair cell death or damage (i.e., noise-induced hearing loss), for instance exposure to a decibel level of at least 85 dB. In some embodiments, the noxious stimulus is age (i.e. age-related hearing loss). In some embodiments, the noxious stimulus is a viral or a bacterial infection of the ear.

Sensory hair cell protective activity of compounds identified using the zebrafish assay of the present invention can be confirmed in in vitro and in vivo model systems known in the art. For instance, the protective or inhibitory activity of identified compounds can be confirmed in vitro using organotypic utricle cultures, for instance, cultured avian, rat, guinea pig or mouse utricles (see, for example, Oesterle, et al. *J Comp Neurol* (2003) 463:177-95; Cunningham, et al., *J Neurosci* (2002) 22:8532-40: Matsui, et al. *J Assoc Res Otolaryngol* (2000) 1:46-63; Kim, et al, *Acta Otolaryngol Suppl* (2004) 551:22-25; and Quint, et al., *Ann NY Acad Sci* (1996) 781: 683-85). In vivo models for use in confirming the protective and inhibitory activities of the identified compounds have been developed in, for example, rats, chinchillas, dogs and primates (see, for example, Guay, et al., *Drug Saf* (1993) 8:350-364); Feghali, et al., *Ear Nose Throat J* (1998) 77:276-285; and Ding, et al., *Ann NY Acad Sci* (1999) 884:152-70). In vivo model systems can be used to confirm the protective and inhibitory activities of the identified compounds against both or either ototoxicity (sensory hair cell damage or death) and nephrotoxicity (renal cell damage or death). All references cited in the foregoing paragraph are hereby incorporated herein by reference.

In one embodiment, the administered identified compound inhibits drug-induced ototoxicity caused by one or more ototoxic pharmacological agents. Oftentimes, an identified compound will protect against sensory hair cell death or damage induced by multiple (i.e., two or more) and distinct ototoxic pharmacological agents, each having a different mechanism of action and distinct therapeutic purpose. In a further embodiment, the administered identified compound protects against ototoxicity induced by one or more pharmacological agents selected from the group consisting of aminoglycosides, anticancer agents, loop diuretics, sesquiterpene lactone endoperoxides, quinines, salicylates, and interferon polypeptides. For instance, in one embodiment the administered identified compound simultaneously protects against aminoglycoside-induced and platinum coordination complex-induced ototoxicity. In one embodiment, the administered identified compound prevents sensory hair cell damage or death caused by neomycin and cisplatin.

In one embodiment, the administered identified compound protects against aminoglycoside-induced ototoxicity. In one embodiment, the administered identified compound protects against sensory hair cell death or damage induced by an aminoglycoside selected from the group consisting of erythromycin, vancomycin, neomycin, gentamicin, streptomycin, kanamycin, tobramycin and amikacin and netilmicin.

In one embodiment, the administered identified compound prevents ototoxicity caused by an anticancer agent, including anticancer agents selected from the group consisting of platinum coordination complexes, nitrogen mustards, vinca alkaloids and DFMO. In one embodiment, the administered identified compound prevents ototoxicity caused by a platinum coordination complex. In one embodiment, the administered identified compound protects against sensory hair cell damage or death caused by cisplatin or carboplatin.

In one embodiment, the administered identified compound inhibits sensory hair cell death or damage caused by a loop diuretic. For instance, in some embodiments, the administered compound protects against ototoxicity induced by a loop diuretic selected from the group consisting of furosemide, bumetanide, ethacrynic acid, torsemide, azosemide, muzolimine, piretanide and tripamide.

In one embodiment, the administered identified compound prevents the ototoxic effects caused by an anti-malarial drug. In certain embodiments, the administered identified compound protects against sensory hair cell death or damage induced by a quinine or a sesquiterpene lactone endoperoxide. In one embodiment, the administered identified compound inhibits ototoxicity caused by a quinine selected from the group consisting of quinine, chloroquine, amodiaquine, hydroxychloroquine, mefloquine, and primaquine, in one embodiment, the administered identified compound prevents sensory hair cell death or damage induced by a sesquiterpene lactone endoperoxide selected from the group consisting of artemisinin, artemether, artesunate, and dihydroartemisinin.

In one embodiment, the administered identified compound protects against salicylate-induced sensory hair cell death or damage. For instance, the administered identified compound prevents ototoxicity caused by a salicylate selected from the group consisting of salicylic acid, acetylsalicylic acid (aspirin), methyl salicylate, diflunisal, salsalate, olsalazine, and sulfasalazine.

The identified compounds are administered to an individual in need thereof. Typically, the identified compounds are administered to a mammal, particularly a domesticated mammal, including mammals of canine, feline, porcine, bovine, ovine, murine, rodentia, and lagomorpha families. Usually, the identified compounds are administered to a human.

Whether treating drug-induced ototoxicity, noise-induced hearing loss, or age-related hearing loss, or other causes of sensory hair cell death or damage, the route of administration for the identified compounds is not critical, so long as the compounds are efficacious in inhibiting or preventing sensory hair cell death or damage. Typically, the identified compounds are formulated for oral administration, but can also be formulated for parenteral administration, for example, intratympanically, topically, subcutaneously, intravenously, intramuscularly. The identified compound also can be prepared in a mixed formulation for co-delivery with an ototoxic drug.

In the case of treating drug-induced ototoxicity, the identified compounds can be administered by the same or by a different route of administration as the ototoxic drug. Preferably, co-administration of an identified compound, either prophylactically or concurrently, does not substantially interfere with the efficacy or therapeutic purpose of the ototoxic drug. The identified compounds also can be prepared in a mixed formulation for co-delivery with an ototoxic drug.

Suitable formulations for use in formulating the identified compounds for administration are found in *Remington: The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art. Generally, an efficacious or effective amount of a compound that decreases, inhibits or prevents sensory hair cell damage or death is determined by first administering a low dose or small amount of the compound, and then incrementally increasing the administered dose or dosages, until a desired effect of decreased, inhibited or prevented sensory hair cell damage or death is observed in the treated subject, with minimal or no toxic side effects. Applicable methods for determining an appropriate dose and dosing schedule for administration of a combination of the present invention are described, for example, in Goodman and Gilman's *The Pharmacological Basis of Therapeutics*, 10th Ed., Hardman, Limbird and Goodman-Gilman, Eds., McGraw-Hill (2001), and in *Remington: The Science and Practice of Pharmacy*, 21$^{st}$ Ed., Gennaro, Ed., Lippencott Williams & Wilkins (2003), both of which are hereby incorporated herein by reference.

Dosage amount and interval can be adjusted individually to provide plasma or local (i.e., intratympanic) levels of the active compounds that are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. Those having skill in the art will be able to optimize therapeutically effective local dosages without undue experimentation.

The following examples are offered to illustrate, not to limit, the present invention.

EXAMPLES

Example 1

Methods for Identifying Protective Compounds

Animals

Zebrafish embryos were produced by paired matings of adult fish maintained at 28.5° C. in the University of Washington zebrafish facility. Beginning at 4 days post fertilization (dpf), larvae were fed live paramecia. Larvae were maintained at a density of 50 per 100 mm$^2$ petri dish in embryo medium (1 mM MgSO$_4$, 120 µM KH$_2$PO$_4$, 74 µM Na$_2$HPO$_4$, 1 mM CaCl$_2$, 500 µM KCl, 15 µM NaCl, and 500 µM NaHCO$_3$ in dH$_2$O) in a tissue incubator at 28.5° C. All animal procedures were approved by the University of Washington institutional Animal Care and Use Committee, Vital Dye Staining Larvae were placed in a transfer device fashioned from a 50 ml conical tube with one end cut off and a mesh cover at the bottom. FM 1-43 (n-(3-triethylammoniumpropyl)-4-(4-dibutylamino]-styryl)pyridinium dibromide; Molecular Probes, Eugene, Oreg.) labeling of lateral line neuromasts was achieved by immersing free swimming larvae in 3 µM FM 1-43 in embryo medium for 30 seconds followed by 3 rinses in embryo medium. Using this procedure FM 1-43 is restricted to hair cells in neuromasts (Seiler and Nicolson, *J Neurobiol* (1999) 41:424-34). Yo-Pro-1 (Molecular Probes, Eugene, Oreg.) labeling of hair cell nuclei in lateral line neuromasts was achieved using a similar technique, incubating larvae in 2 µM Yo-Pro-1 in embryo medium for 30 minutes followed by 3 rinses. Using this procedure only the nuclei of hair cells are labeled.

Screen

Zebrafish eggs of the AB/Wik wild-type strain were generated and maintained until 5 days post-fertilization temporally corresponding to the developmental maturation of the lateral line hair cells. 5 day postfertilization larvae were prelabeled with the fluorescent dyes FM 1-43, 3 µM (30 sec), and Yo-Pro-1, 2 µM (30 min) to identify the hair cells. Larvae were arrayed into 96 well plates containing embryo media. Synthetic small molecules from the Chembridge Corporation, San Diego, were transferred into the wells for a final concentration of 10 µM (0.05% DMSO). Following a one hour exposure to the compounds fish were treated with neomycin for an additional hour. Larvae were then analyzed in vivo with an epifluorescent Zeiss Axiovert 200M microscope with automated stage and a 40× objective to determine hair cell viability following neomycin exposure.

Neomycin Treatment

Neomycin sulfate from a 50 mM stock solution in $dH_2O$ (Sigma) was diluted in embryo medium to final concentrations of 25 µM, 50 µM, 100 µM, 200 µM and 400 µM in each well of a six-well culture plate. Following vital dye staining live free-swimming five dpf larvae were transferred from control (neomycin-free) embryo medium to neomycin-containing medium and incubated for 1 h. For time-lapse imaging, neomycin-containing medium was added directly to the imaging chamber.

Cisplatin Treatment

Cisplatin from a 200 mM stock solution in DMSO (Sigma) was diluted in embryo medium to final concentrations of 300 µM, 500 µM, and 1 mM (0.05% DMSO) in each well of a six-well culture plate. Following vital dye staining live free-swimming five dpf larvae were transferred from control (neomycin-free) embryo medium to cisplatin-containing medium and incubated for 3 h.

Example 2

Identification of Long-Lasting Protective Compounds that do Not Inhibit

Figure 1A:
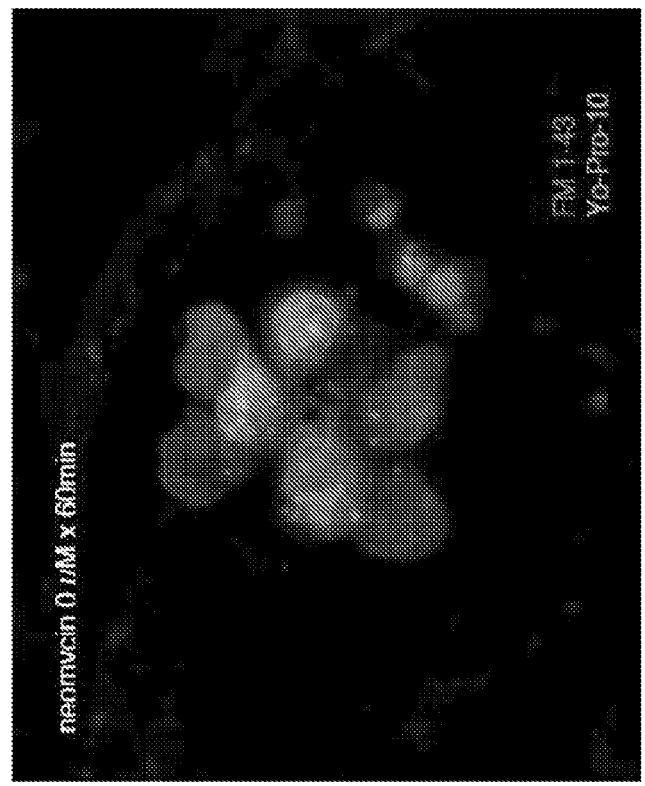
Figure 2:
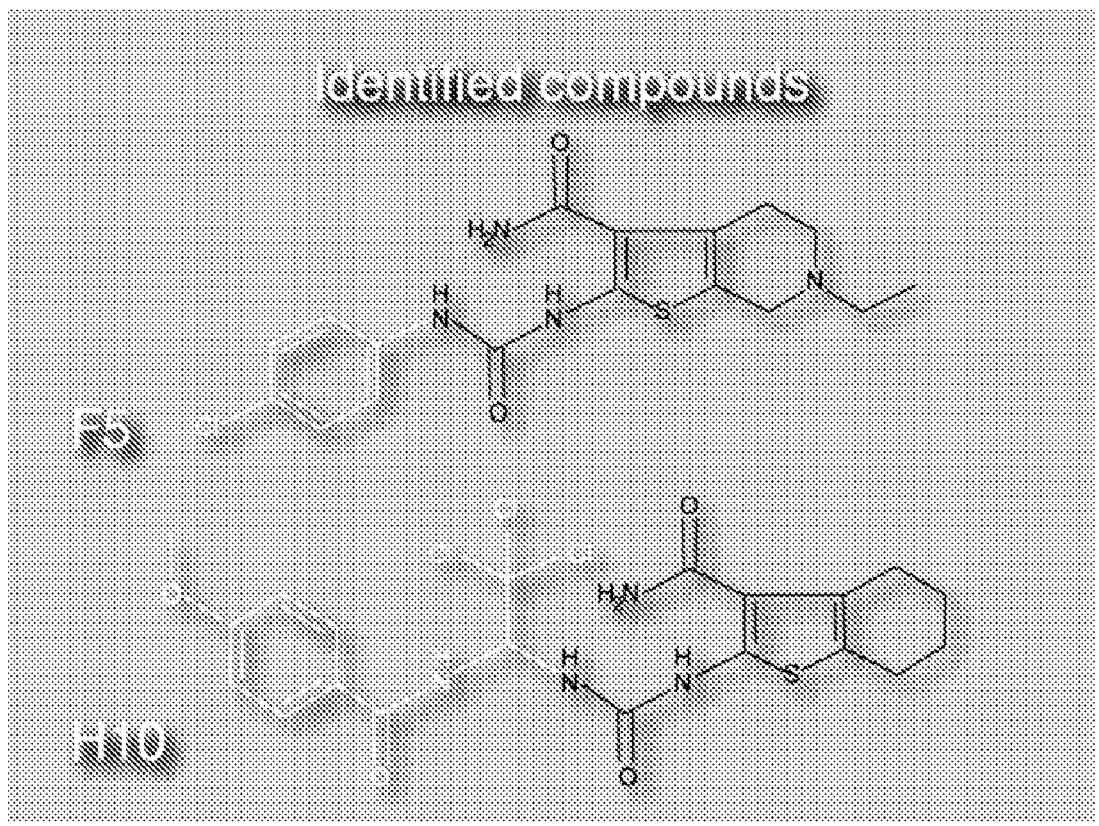
FIG. 2 illustrates compounds F5 and H10, structurally related compounds identified using the present methods and which protect hair cells from the aminoglycoside neomycin.

Use of Small Molecule Screens to Identify Otoprotective Compounds Using the Lateral Line Hair Cells of Zebrafish In order to identify compounds that protect hair cells of the lateral line from the toxic effects of the aminoglycoside neomycin, 10,960 small molecules were screened. 5 dpf larvae were double labeled with the fluorescent dyes FM 1-43 and Yo-Pro-1, pretreated with the compounds at a dose of 10 µm, exposed to 200 mM neomycin, and their hair cells evaluated after 1 hour, FIG. 1.

Two (2) of 10,960 compounds were identified in the screen to protect hair cells from neomycin induced hair cell death, 2-({[(4-chlorophenyl)amino]carbonyl}amino)-6-ethyl-4,5,6,7-tetrahydrothieno[2,3-c]pyridine-3-carboxamide (C17 H19 Cl N4 O2 S) (F5) and 2-{[({2,2,2-trichloro-1-[(4-methoxybenzoyl)amino]ethyl}amino)carbonothioyl]amino}-4,5,6,7-tetrahydro-1-benzothiophene-3-carboxamide (C20 H21 Cl3 N4 O3 S2) (H10). F5 and H10 are structurally similar small molecules.

Compounds F5 and H10 Attenuate Aminoglycoside Induced Hair Cell Death

Figures 3A, 3B:
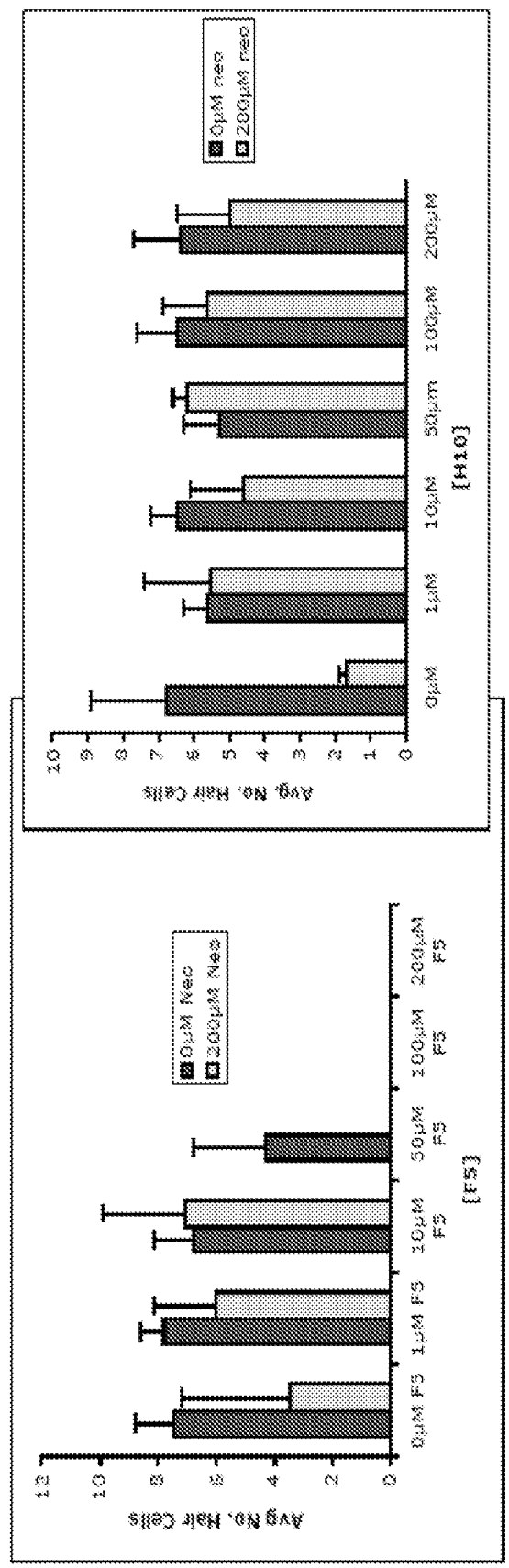
FIG. 3A illustrates how F5 is optimally protective against 200 µm neomycin at 1 µM.
FIG. 3B shows that H10 is optimally protective against 200 µM neomycin at 1 µM.

To identify the optimal dose for evaluating the compounds' protective effects, larvae were pretreated with both compounds at 0, 1, 10, 50, 100 and 200 µM, and exposed to neomycin at 200 µM and compared to controls. Compounds F5 and H10 were both protective against neomycin. Optimal protection against 200 µM neomycin was observed with 10 µM F5 and 1 µM H10, FIG. 3.

Figure 4:
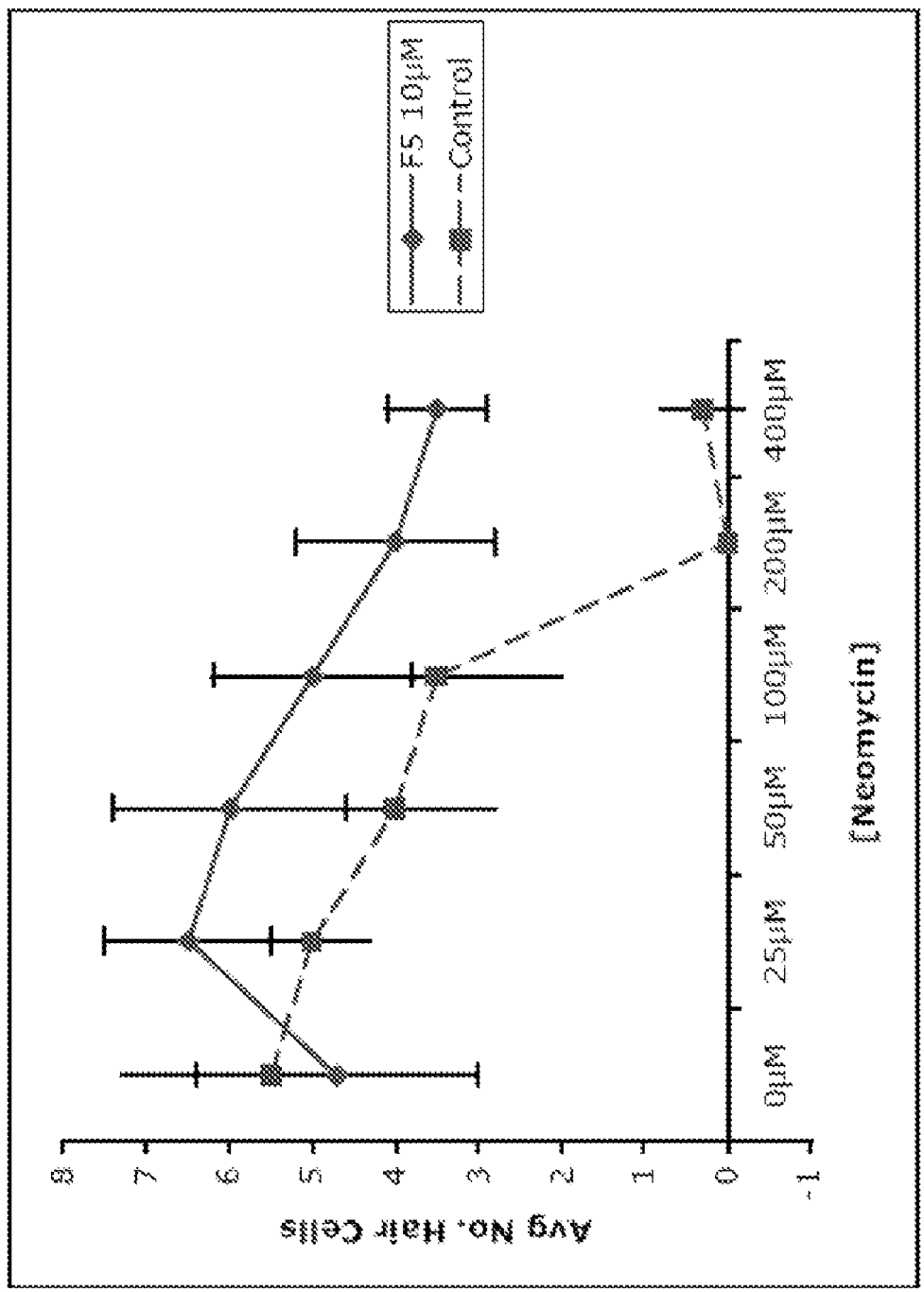
FIG. 4 illustrates how F5 protects lateral line hair cells against neomycin.

The neomycin susceptibility of larvae pretreated with 10 µM of compound F5 and controls at 0, 25, 100, 200 and 400 µm neomycin were compared. Larvae pretreated with compound F5 were less susceptible to neomycin than controls, FIG. 4.

The Protection Conferred by Compounds F5 and H10 is Long Lasting.

Figure 5:
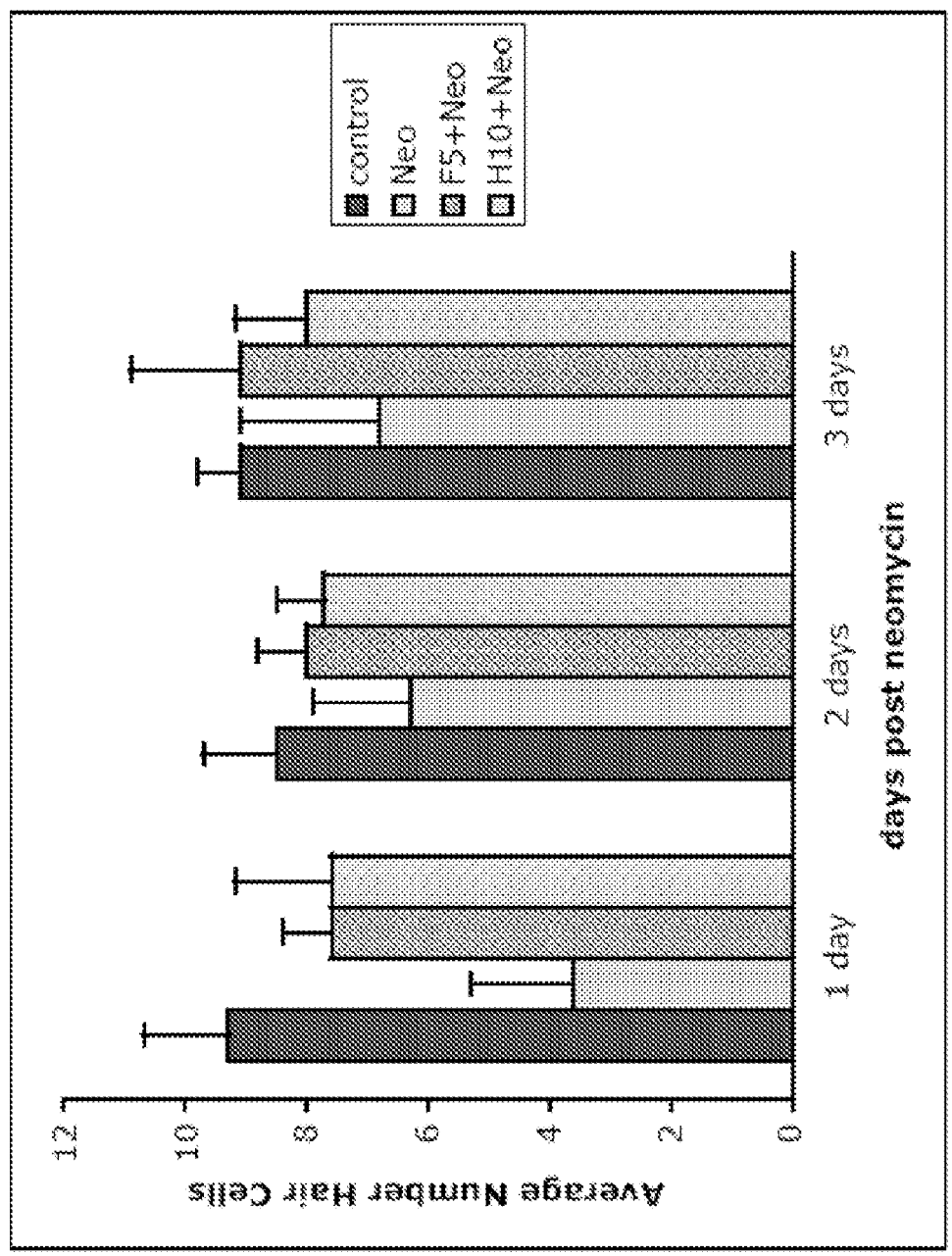
FIG. 5 illustrates how F5 and H10 are protective through 24 hours post neomycin treatment. Hair cell regeneration in the lateral line prevents evaluation beyond this time.
Figure 6:
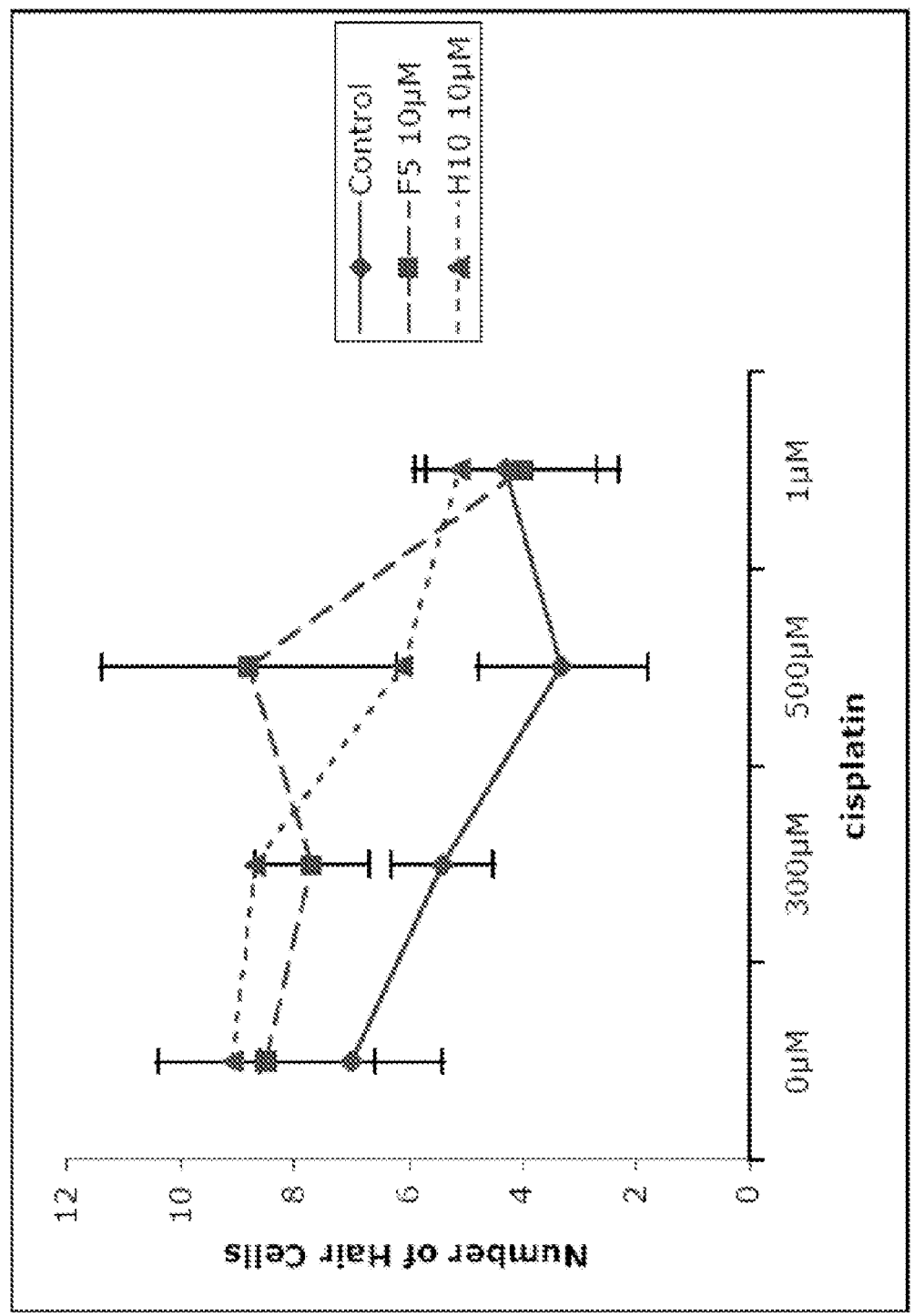
FIG. 6 illustrates how pretreatment with F5 is protective against cisplatin-induced lateral Sine hair cell death.

To evaluate the protection conferred by compounds F5 and H10, hair cell counts were compared using the fluorescent dye FM 1-43 to identify hair cells in larvae pretreated with compound and controls, exposed to 200 µm neomycin after 24 hours, 48 hours and 72 hours. Significant protection was readily identified at 24 hours. At 48 hours and beyond the protective effects of compound F5 and H10 cannot be determined as the larvae have repopulated the neuromasts with regenerated hair cells, FIG. 5.

Compound F5 Attenuates Cisplatin-Induced Hair Cell Death.

Figure 8:
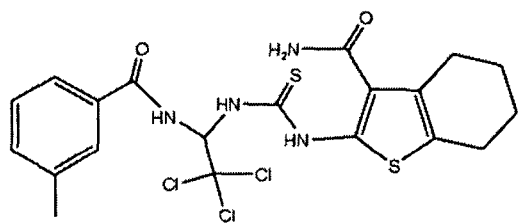
FIG. 8 illustrates additional compounds identified using the present screening methods.
Figure 8:
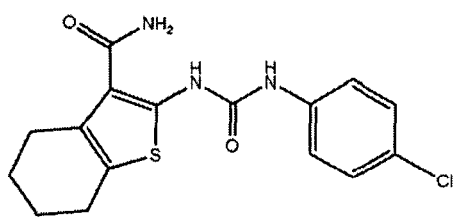
Figure 8:
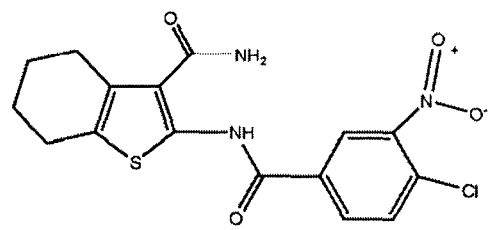
Figure 8:
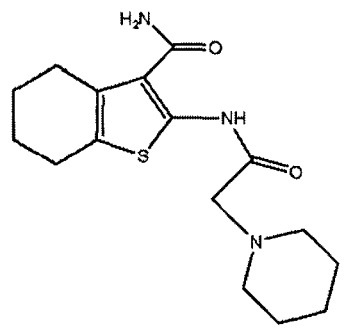

To determine if compound F5 is protective against the otoxic effects of cisplatin, larvae were pretreated with compound F5 10 µm for 1 hour, exposed the larvae to 0, 300 µM, 500 µM and 1 mM of cisplatin for 3 hours, counted hair cells and compared to untreated controls. Compound F5 shows significant protection against cisplatin induced hair cell death, FIG. 8.

Compounds F5 and H10 do not Inhibit Mechanotransduction-Dependent Activity of Lateral Line Hair Cells as Measured by FM 1-43 Uptake.

Figure 7:
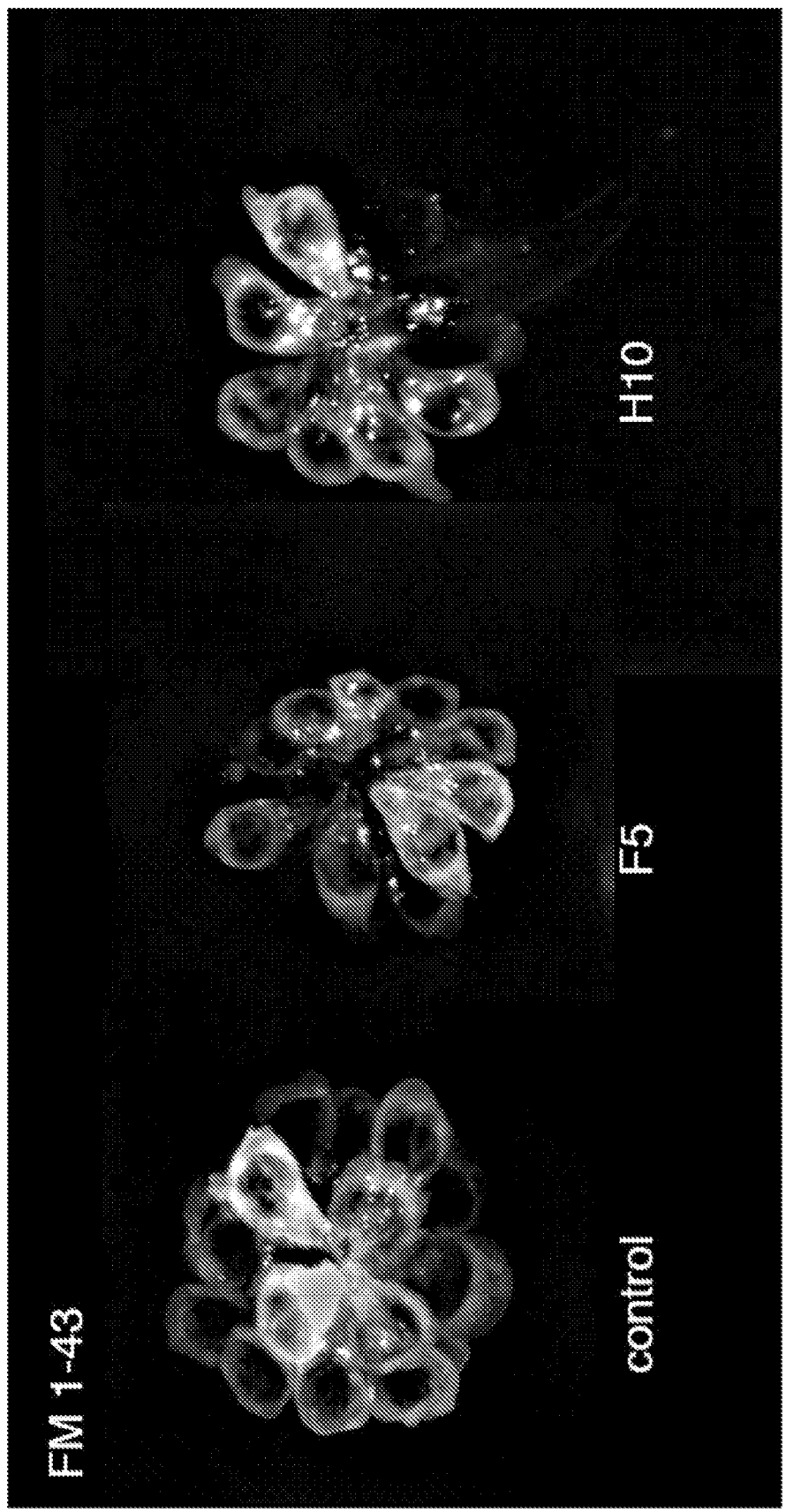
FIG. 7 illustrates how compounds F5 and H10 do not prevent the rapid uptake of FM1-43.

To test whether compounds F5 and H10 inhibit mechanotransduction-dependent activity of lateral line hair cells, larvae were incubated in the dye FM1-43. Larvae were pretreated with each compound for 1 hour at 10 µm and exposed to FM 1-43, 3 µM, for 30 seconds. For this brief time period, FM 1-43 uptake has been shown to be taken up my mechanotransduction-dependent activity in zebrafish (Sidi et al. *Science* (2003) 301:96-99). Neither compound F5 nor compound H10 inhibited the uptake of FM1-43, FIG. 7. Compounds F5 and H10 do not inhibit mechanotransduction-dependent activity as measured by FM-1-43 uptake.

Example 3

FDA-Approved Protective Compounds Identified Via High-Throughput Screening

A library of 1040 FDA approved compounds (NINDS Custom Collection II, Microsource, Inc.) were screened using a high-throughput assay. This screen identified seven drugs that protect against aminoglycoside-induced hair cell death.

1. Cepharanthine is a biscoclaurine alkaloid from Stephania cepharantha. It is thought to have membrane-stabilizing activity and has been used for the treatment of nasal allergy and snake venom-induced hair cell death,
2. Amsacrine is an acridine dye derivative that is thought to inhibit topoisomerase II and cause DNA strand breaks.
3. Drofenine is an anticholinergic drug that acts on smooth muscles and is used as an antispasmodic. It acts on M1 and M2 muscarinic receptors and also has been shown to have inhibitory effects on butyrylcholinesterase.
4. Phenoxybenzamine is an alpha-adrenergic blocker used for hypertension.
5. N,N-hexamethyleneamiloride is a blocker of Na/H exchange.

6. Carvedilol is a nonselective beta-adrenergic blocker with alpha-1 blocking activity and is used for the control of hypertension and for the treatment of heart failure.
7. 9-amino-1,2,3,4-tetrahydroacridine is an acetylcholinesterase inhibitor that has been used in the treatment of Alzheimer's disease.

The protective effects of these seven drugs have been confirmed by dose response curves. While each drug has known biologic activity and is approved for certain clinical applications, their use as otoprotectants has not been described in the literature. Because these drugs have already been approved by the FDA for other uses, they have been demonstrated as safe for use in humans.

It is understood that the examples and embodiments described herein are for illustrative purposes only and that various modifications or changes in light thereof will be suggested to persons skilled in the art and are to be included within the spirit and purview of this application. All publications, patents, and patent applications cited herein, including U.S. provisional patent application No. 60/655,463, filed Feb. 22, 2005, are hereby incorporated by reference in their entirety for all purposes.

What is claimed is:

1. A method of preventing a condition associated with sensory hair cell death associated with aminoglycoside treatment, the method comprising administering a sufficient amount of a compound selected from the group consisting of:

2-({[(4-chlorophenyl)amino]carbonyl}amino)-6-ethyl-4,5,6,7-tetrahydrothieno[2,3-c]pyridine-3-carboxamide (F5), 2-{[({2,2,2-trichloro-1-[(4-methoxybenzoyl)amino]ethyl}amino)carbonothioyl]amino}-4,5,6,7-tetrahydro-1-benzothiophene-3-carboxamide (C20 H21 Cl3 N4 O3 S2) (H10),

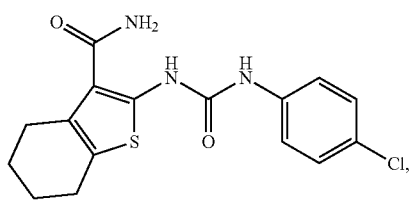

Compound B

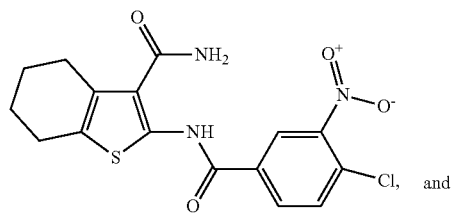

Compound C

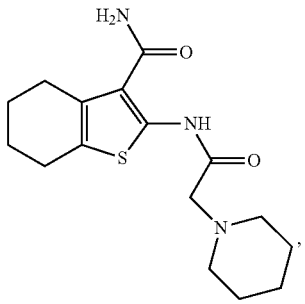

Compound D and mixtures thereof, wherein said compound inhibits lateral line hair cell death in a zebrafish.

2. The method of claim 1, wherein said compound is F5.

3. The method of claim 1, wherein said compound is H10.

4. The method of claim 1, wherein said compound is administered prior to exposure to a noxious stimulus that induces ototoxicity.

5. The method of claim 1, wherein said compound is administered at the same time as exposure to a noxious stimulus that induces ototoxicity.

6. The method of claim 1, wherein said compound is administered after exposure to a noxious stimulus that induces ototoxicity.

7. A method of inhibiting sensory hair cell death associated with aminoglycoside treatment, the method comprising administering a sufficient amount of a compound selected from the group consisting of:

2-({[(4-chlorophenyl)amino]carbonyl}amino)-6-ethyl-4,5,6,7-tetrahydrothieno[2,3-c]pyridine-3-carboxamide (F5), 2-{[({2,2,2-trichloro-1-[(4-methoxybenzoyl)amino]ethyl}amino)carbonothioyl]amino}-4,5,6,7-tetrahydro-1-benzothiophene-3-carboxamide (C20H21Cl3 N4 O3 S2) (H10), and

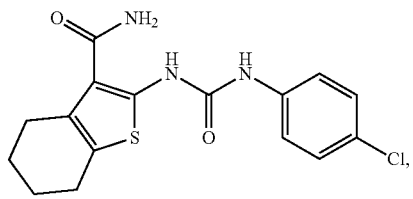

Compound B

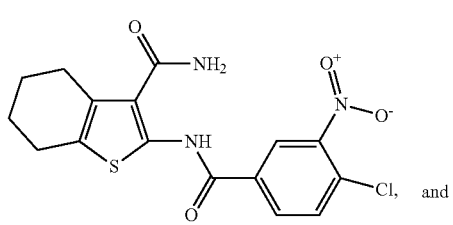

Compound C

Compound D

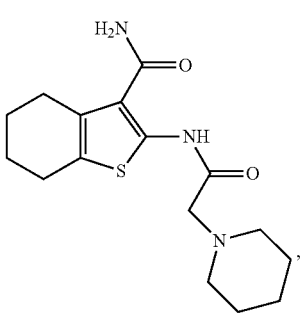

and mixtures thereof, wherein said compound inhibits lateral line hair cell death in a zebrafish.

8. The method of claim 7, wherein said compound is F5.

9. The method of claim 7, wherein said compound is H10.

10. The method of claim 7, wherein said compound is administered prior to exposure to a noxious stimulus that induces ototoxicity.

11. The method of claim 7, wherein said compound is administered at the same time as exposure to a noxious stimulus that induces ototoxicity.

12. The method of claim 7, wherein said compound is administered after exposure to a noxious stimulus that induces ototoxicity.

13. The method of claim 1, wherein said compound is administered to an individual by oral or parenteral administration.

14. The method of claim 7, wherein said compound is administered to an individual by oral or parenteral administration.

15. A method of inhibiting sensory hair cell death associated with aminoglycoside treatment in an individual, the method comprising administering to the individual a sufficient amount of 2-({[(4-chlorophenyl)amino]carbonyl}amino)-6-ethyl-4,5,6,7-tetrahydrothieno[2,3-c]pyridine-3-carboxamide (F5).

* * * * *